United States Patent
Kaiser et al.

(10) Patent No.: US 10,959,629 B2
(45) Date of Patent: Mar. 30, 2021

(54) MULTISENSOR CARDIAC STROKE VOLUME MONITORING SYSTEM AND ANALYTICS

(71) Applicant: THE REGENTS OF THE UNIVERSITY OF CALIFORNIA, Oakland, CA (US)

(72) Inventors: William Kaiser, Los Angeles, CA (US); Nils Peter Borgstrom, Los Angeles, CA (US); Per Henrik Borgstrom, Charlestown, MA (US); Aman Mahajan, Sherman Oaks, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 131 days.

(21) Appl. No.: 16/102,702

(22) Filed: Aug. 13, 2018

(65) Prior Publication Data

US 2019/0059747 A1   Feb. 28, 2019

Related U.S. Application Data

(60) Provisional application No. 62/552,850, filed on Aug. 31, 2017.

(51) Int. Cl.
*A61B 5/029* (2006.01)
*A61B 5/00* (2006.01)
(Continued)

(52) U.S. Cl.
CPC .......... *A61B 5/029* (2013.01); *A61B 5/0024* (2013.01); *A61B 5/02028* (2013.01);
(Continued)

(58) Field of Classification Search
CPC ... A61B 5/029; A61B 5/0024; A61B 5/02028; A61B 5/04012; A61B 5/04085;
(Continued)

(56) References Cited

U.S. PATENT DOCUMENTS

| | | | | |
|---|---|---|---|---|
| 8,515,201 B1* | 8/2013 | Murray Herrera | .... | G06K 9/527 382/100 |
| 2003/0144702 A1 | 7/2003 | Yu | | |

(Continued)

OTHER PUBLICATIONS

ISA/US, United States Patent and Trademark Office (USPTO), International Search Report and Written Opinion dated Oct. 19, 2018, related PCT international application No. PCT/US2018/046575, pp. 1-9, claims searched, pp. 10-13.
(Continued)

*Primary Examiner* — Erin M Piateski
(74) *Attorney, Agent, or Firm* — O'Banion & Ritchey LLP; John P. O'Banion

(57) ABSTRACT

An Integrated CardioRespiratory (ICR) System is provided for continuous Stroke Volume (SV) measurement using a wearable device comprising a plurality of acoustic sensors. The ICR system performs signal processing computations to characterize cardiac acoustic signals that are generated by cardiac hemodynamic flow, cardiac valve, and tissue motion, and may use advanced machine learning methods to provide accurate computation of SV.

29 Claims, 10 Drawing Sheets

(51) Int. Cl.
*A61B 5/02* (2006.01)
*A61B 5/0456* (2006.01)
*A61B 5/0408* (2006.01)
*A61B 7/02* (2006.01)
*A61B 5/04* (2006.01)

(52) U.S. Cl.
CPC ........ *A61B 5/04012* (2013.01); *A61B 5/0456* (2013.01); *A61B 5/04085* (2013.01); *A61B 5/7267* (2013.01); *A61B 7/026* (2013.01); *A61B 5/6823* (2013.01); *A61B 5/6831* (2013.01); *A61B 5/7203* (2013.01); *A61B 5/725* (2013.01); *A61B 5/7257* (2013.01); *A61B 5/7264* (2013.01); *A61B 7/02* (2013.01); *A61B 2562/0204* (2013.01); *A61B 2562/04* (2013.01); *A61B 2562/046* (2013.01)

(58) Field of Classification Search
CPC ..... A61B 5/0456; A61B 5/7267; A61B 7/026; A61B 7/04; A61B 5/6823; A61B 5/6831; A61B 5/7203; A61B 5/725; A61B 5/7257; A61B 5/7264; A61B 7/02; A61B 2562/0204; A61B 2562/04; A61B 2562/046

USPC .......................................................... 600/526
See application file for complete search history.

(56) References Cited

U.S. PATENT DOCUMENTS

| | | |
|---|---|---|
| 2003/0208240 A1 | 11/2003 | Pastore |
| 2008/0001735 A1* | 1/2008 | Tran ....................... G06F 19/00 340/539.22 |
| 2009/0209875 A1 | 8/2009 | Giorgis |
| 2014/0094870 A1 | 4/2014 | Renesto |
| 2016/0019914 A1* | 1/2016 | Sugiyama ............ A61B 5/7235 381/56 |
| 2018/0168473 A1* | 6/2018 | Du ........................ A61B 5/6833 |
| 2019/0133516 A1* | 5/2019 | Banet ................... A61B 5/0295 |

OTHER PUBLICATIONS

ISA/US, United States Patent and Trademark Office (USPTO), International Search Report and Written Opinion dated Oct. 24, 2018, related PCT international application No. PCT/US2018/046378, pp. 1-10, claims searched, pp. 11-16.

* cited by examiner

Discrete Time Steps

Discrete Time Steps

Discrete Time Steps

Discrete Time Steps

Discrete Time Steps

Discrete Time Steps

MULTISENSOR CARDIAC STROKE VOLUME MONITORING SYSTEM AND ANALYTICS

CROSS-REFERENCE TO RELATED APPLICATIONS

This application claims priority to, and the benefit of, U.S. provisional patent application Ser. No. 62/552,850 filed on Aug. 31, 2017, incorporated herein by reference in its entirety.

STATEMENT REGARDING FEDERALLY SPONSORED RESEARCH OR DEVELOPMENT

Not Applicable

NOTICE OF MATERIAL SUBJECT TO COPYRIGHT PROTECTION

A portion of the material in this patent document may be subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to patient monitoring, and more particularly to monitoring cardiac stroke volume.

2. Background Discussion

A critical need has emerged for heart function monitoring to enable constant vigilant monitoring of patients who are at risk due to Congestive Heart Failure (CHF). Over 5 million Americans suffer from CHF which accounts for over one in 9 deaths in the U.S. Acute worsening of cardiac function is one of the most common causes for admission to hospital treatment and the leading contributor to healthcare delivery cost. An urgent and unmet need exists for continuous, non-invasive monitoring of heart function that can reduce the burden of heart disease through identification of patients at risk and opportunity for early prevention and intervention of disease conditions. Past technology solutions have focused on monitoring only of the Electrocardiography (ECG) signal sources. However, the critical biomechanical function of the heart is not monitored, thus limiting the nature of the assessment.

Current methods for measuring SV include point in time assessment with advanced echocardiography technology and MRI systems along with methods including Radionuclide Ventriculography or Radionuclide Angiography. However, these methods are costly in application, require presence and support of expert technicians, and are not capable of continuous monitoring.

BRIEF SUMMARY

An important diagnostic indicator of CHF condition is the measurement of left ventricle Stroke Volume (SV) corresponding to the blood volume delivered by the heart during each heart beat event. The related value of Cardiac Output is the product of SV with heart rate. Low values of SV are indicative of a CHF condition] and provide a data point required for determining patient care. Large decreases in SV indicate risk of mortality.

Accordingly, an aspect of the present technology is an Integrated CardioRespiratory (ICR) System that enables continuous SV measurement with a wearable device providing clinicians with the most critical assessment metric for patient care. In a preferred embodiment, the ICR system performs signal processing computations to characterize cardiac acoustic signals that are generated by cardiac hemodynamic flow, cardiac valve, and tissue motion. In another embodiment, signal processing is accompanied with advanced machine learning methods to provide accurate computation of SV.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

1. Introduction

One of the most important diagnostic indicators of CHF condition is the measurement of left ventricle Stroke Volume (SV) corresponding to the blood volume delivered by the heart during each heart beat event. The related value of Cardiac Output is the product of SV with heart rate. Low values of SV indicate a CHF condition presence and provide a data point required for determining patient care. Large decreases in SV indicate risk of mortality. This risk is not indicated by other measurements, including ECG, as these methods do not directly measure heart function.

The ICR system described herein enables continuous SV measurement with a wearable device providing clinicians with the most critical assessment metric for patient care. Specifically, the ICR system applies compact, wearable acoustic sensor devices and ECG sensor electrodes in a convenient patient belt or adhesive attachment application system. The ICR system performs signal processing computation to characterize heart sound signals that are generated by cardiac hemodynamic flow, cardiac valve, and tissue motion. Signal processing is accompanied with advanced machine learning methods to provide accurate computation of SV.

The ICR system beneficially provides clinical patient care via continuous and convenient monitoring ensuring patient safety with benefits to patients and clinicians as well as hospital facilities that can advance fundamental care. The ICR system beneficially is also advantageous for outpatient treatment by providing cardiac function monitoring to patients who otherwise will not receive assessment. Finally, the ICR system beneficially is further advantageous in residential monitoring, providing an unprecedented heart function remote diagnostic capability enabling early intervention and advanced perioperative care delivery.

2. ICR System Components

Figure 1:
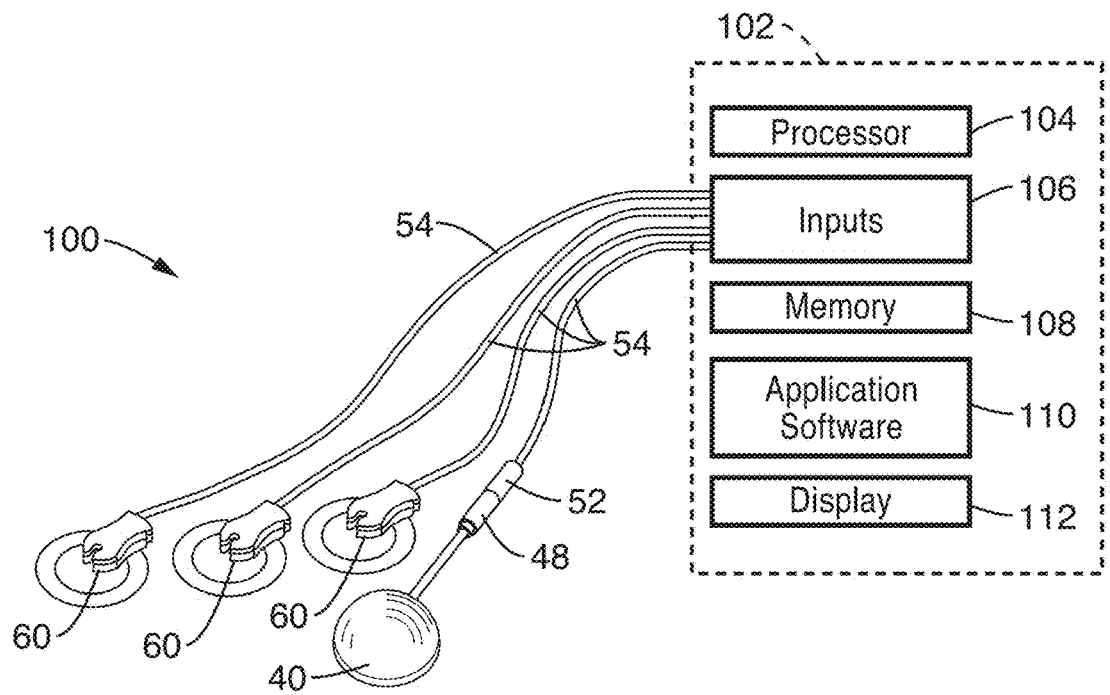
FIG. 1 shows a schematic diagram of the ICR monitoring system of the present description.

In a preferred embodiment illustrated in FIG. 1, the ICR monitoring system 100 generally employs the following components: ICR acoustic sensors 40, ECG sensor electrodes 60; and an ICR patient monitor 102. Monitor 102 comprises inputs 106 for receiving signals from ICR acoustic sensors 40 and ECG sensor electrodes 60 via leads 54. Application programming 110 is provided within memory 108 for analyzing data from ICR acoustic sensors 40 and ECG sensor electrodes 60 via execution on processor 104. Patient monitor 102 may also comprise a display 112 for outputting computed analysis results.

Figure 2A:
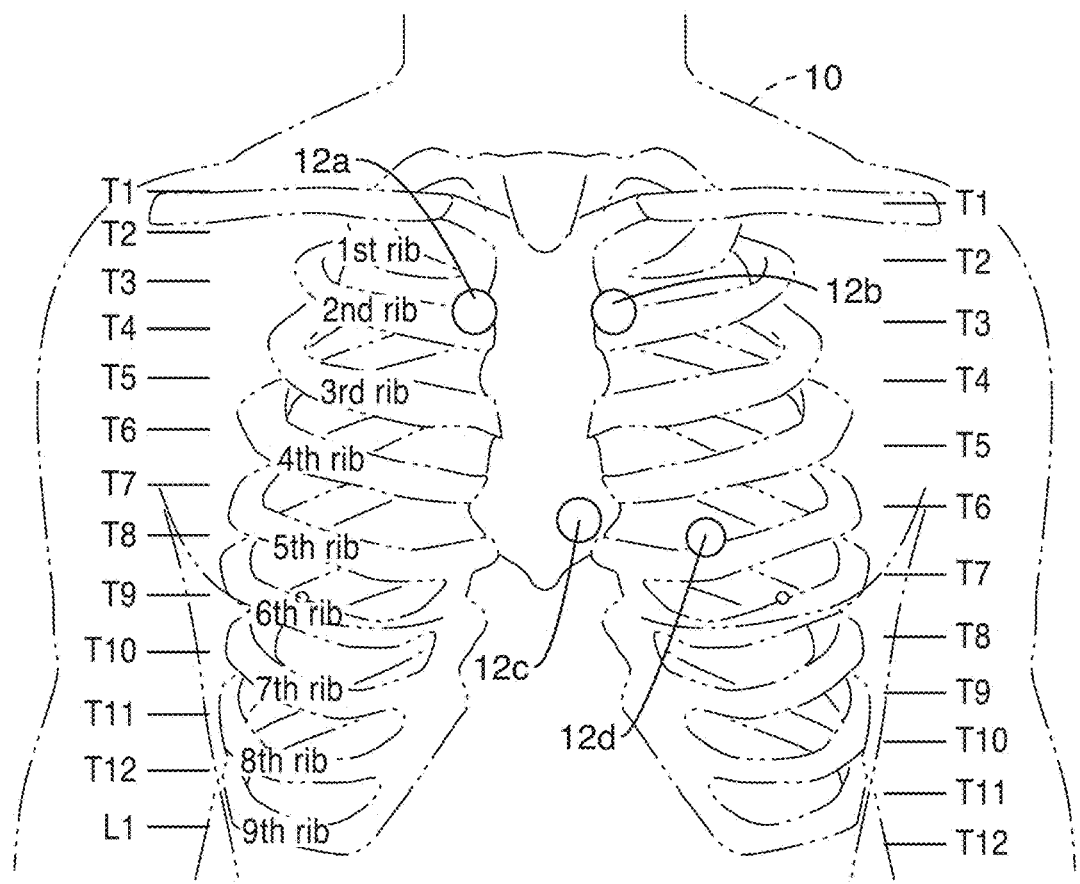
FIG. 2A shows an image of representative ICR acoustic sensor locations based on typical auscultatory sites used with standard stethoscope system.
Figure 3:
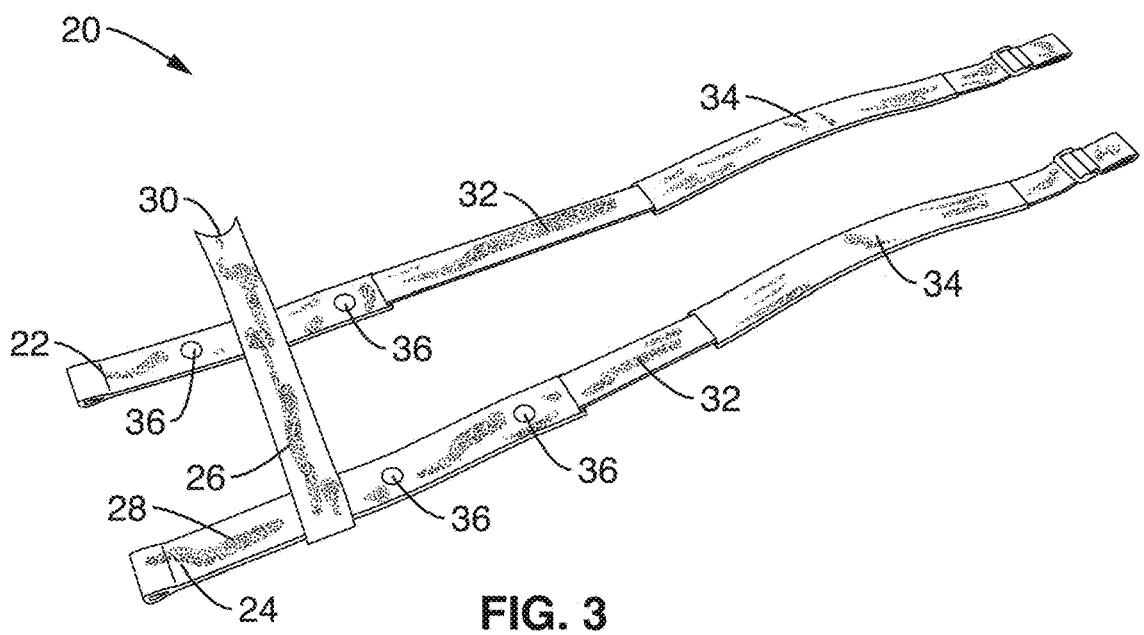
FIG. 3 illustrates a schematic diagram of an embodiment of the ICR sensor support without acoustic sensors.
Figure 4:
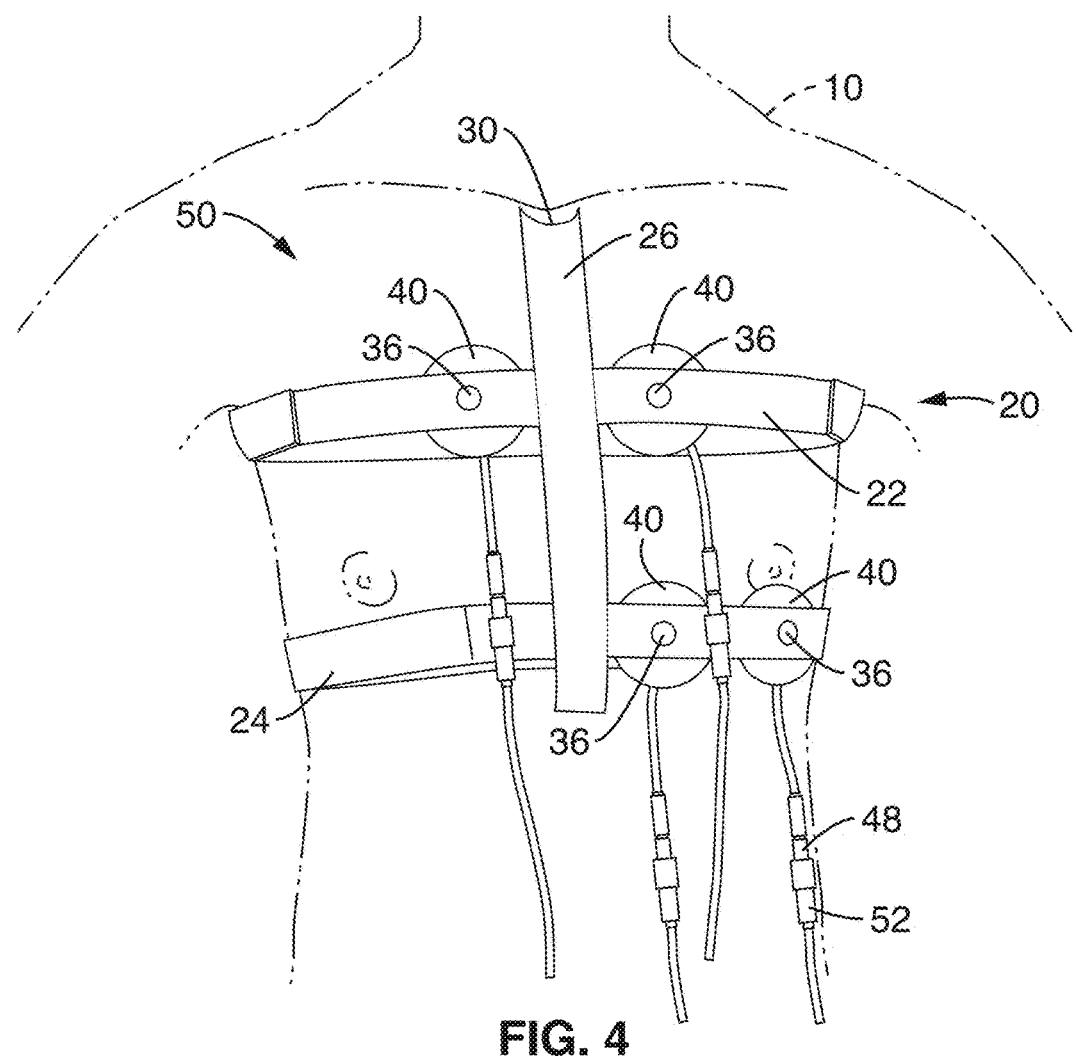
FIG. 4 illustrates a schematic diagram of the ICR sensor support with multiple acoustic sensors to form an ICR sensor application system positioned around the abdomen of the patient.

One ICR acoustic sensor 40 is shown in FIG. 1, however as shown in FIG. 3 and FIG. 4, multiple acoustic sensors 40 may be employed with ICR sensor support 20 to form an ICR sensor application system 50. As will be explained in further detail below, ICR sensor support 20 is configured to support ICR acoustic sensors 40 on the body of the patient 10 at locations based on typical auscultatory sites (FIG. 2A) used with standard stethoscope system, e.g. aortic site location 12a, pulmonary site location 12b, tricuspid site location 12c and mitral site location 12d.

Figure 2B:
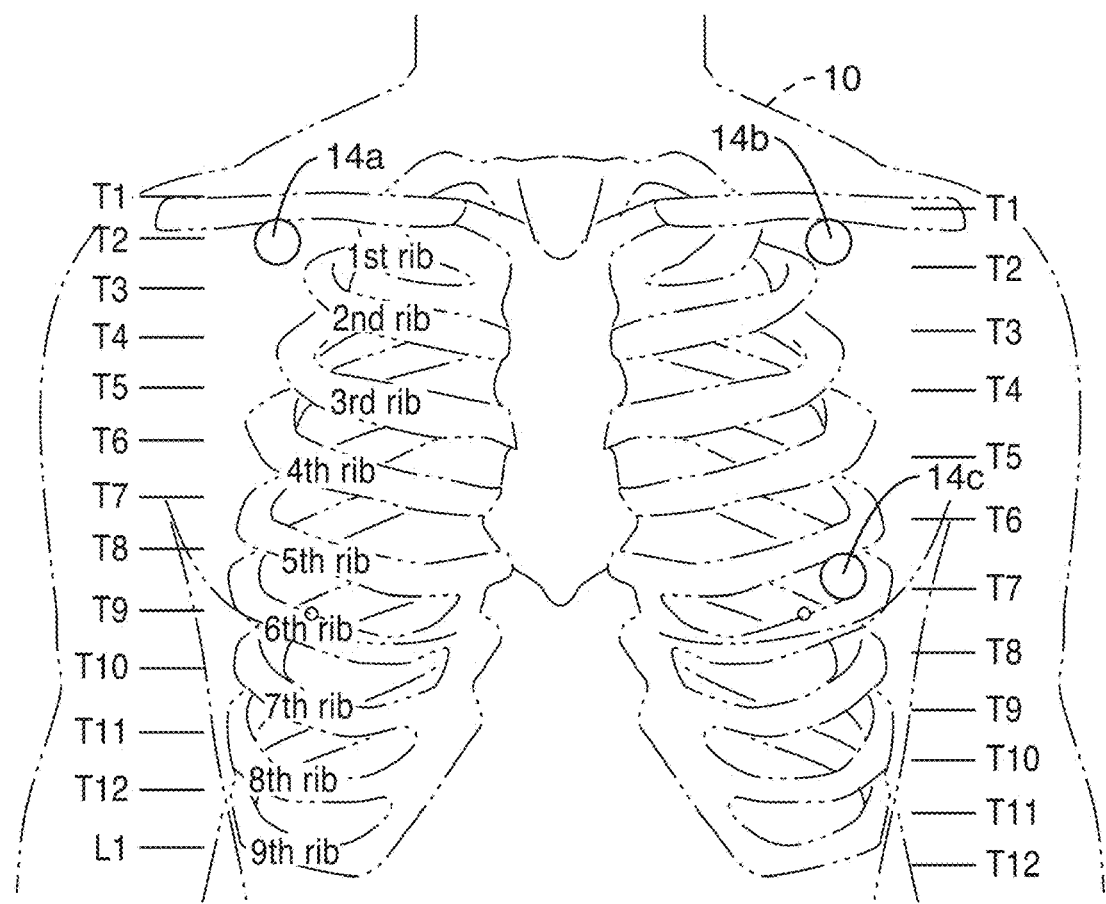
FIG. 2B shows an image of representative ECG sensor electrodes locations applied at conventional RA, LA, and LL monitoring sites.

In one embodiment, the ICR monitoring system 100 includes measurement capability for the ICR acoustic sensors 40 and standard three-lead, optically-isolated, ECG measurement. FIG. 2B shows an image of representative ECG sensor electrode 60 locations 14a, 14b, and 14c applied at conventional RA, LA, and LL monitoring sites, respectively.

In one embodiment, the ICR monitoring system 100 measures both acoustic signals from the four measurement sites 12a through 12d as well as the ECG signal from ECG sites 14a through 14c. Computation of SV is based on analysis of the S1 and S2 characteristics and the time of arrival of S1 and S2 events relative to the QRS event in the ECG signal as explained in further detail below.

In an alternative embodiment, the ICR monitoring system is configured to monitor only acoustic signals from the ICR acoustic sensors 40 using a PCG-gated segmentation method, as provided in further detail below. In such system, ECG sensors, or other sensor input, are not necessary.

2.1 ICR Sensor Application System

In a preferred embodiment shown in FIG. 3 and FIG. 4, the ICR sensor support 20 of FIG. 3 is placed around the upper abdomen of a patient 10 with ICR acoustic sensors 40 to form an ICR sensor application system 50. The ICR sensor application system 50 holds ICR acoustic sensors 40 in position (e.g. at auscultatory locations 12a-12d) to allow for continuous signal recording in a form that is comfortable for the patient, convenient and accurate for the care provider, and provides a low-cost disposable component enabling single-use.

FIG. 3 illustrates an embodiment of the ICR sensor support 20 without acoustic sensors 40. The ICR sensor support 20 includes two chest straps 22, 24 that are configured to be positioned horizontally around the patient. A vertical separator component 26 is fixed to the upper chest strap 22 and is configured to be releasably attached via a releasable fastener 28 (e.g. hook-and-loop) to the lower chest strap 24. The vertical separator component 26 coupling the two chest straps 22, 24 indicates the vertical position of the straps. A small semicircular indicator 30 at the upper end of the vertical separator 26 indicates the familiar and easily identified suprasternal notch of the sternum. The chest straps 22, 24 each include a pair of markers 36 that are configured to locate attachment of the ICR acoustic sensors 40 individually at preferred locations for acoustic monitoring within the abdomen/chest of the patient 10.

Each of the chest straps 22, 24 include flexible stiffener sections 34 and elastic sections 32 for application convenience. All materials, including the elastic sections 32, are preferably composed of latex-free, biocompatible materials.

In one embodiment, the ICR sensor support 20 is provided in a kit of varying sizes to match varying patient size, e.g. 5 sizes labeled X-Small, Small, Medium, Large, and X-Large. These sizes may be selected according to subject height according to Table 1.

FIG. 4 illustrates the ICR sensor support 20 with four acoustic sensors 40 to form an ICR sensor application system 50 positioned around the abdomen of the patient 10. With the semicircular indicator 30 at the upper end of the vertical separator 26 positioned at suprasternal notch of the sternum, the ICR acoustic sensors 40 are aligned at the proper locations for acoustic sensing, e.g. ICR acoustic sensors 40 on the upper chest strap 22 are aligned with the aortic site location 12a and pulmonary site location 12b, while the ICR acoustic sensors 40 on the lower chest strap 24 are aligned with tricuspid site location 12c and mitral site location 12d.

In one embodiment, the ICR sensor support 20 and/or ICR sensor application system 50 are configured as a disposable, single-use device ensuring proper and convenient attachment as well as patient comfort. In the embodiment shown in FIG. 4, identical acoustic sensors 40 are shown applied to a subject. Each of the acoustic sensors 40 may have male 48/female 52 lead connections that are color coded for attachment to the ICR patient monitor via leads 54.

Figure 5:
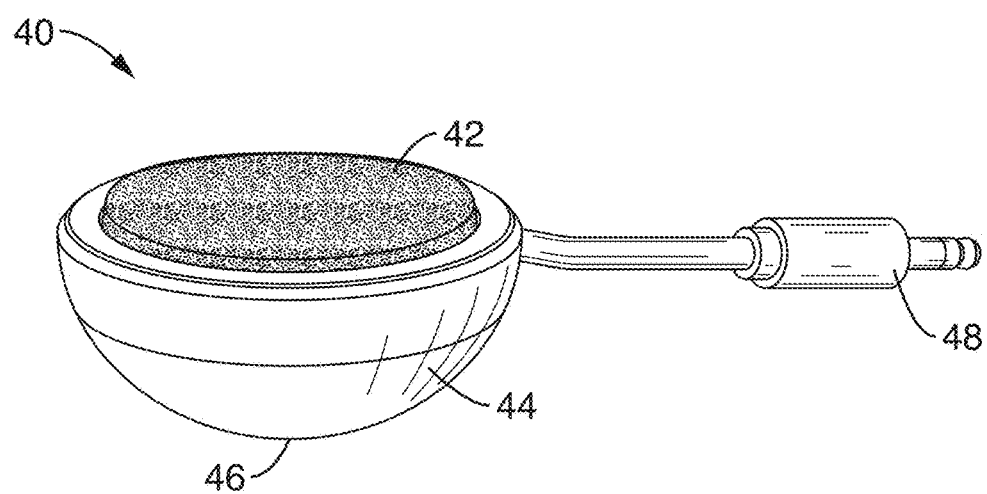
FIG. 5 shows a side view of an ICR acoustic sensor in accordance with the present description.

FIG. 5 shows a side perspective view of an exemplary ICR acoustic sensor 40 in accordance with the present description. ICR acoustic sensor 40 comprises a half-dome shaped housing 44 with a nitrile (latex-free) membrane 42. At the opposite end 46 of the housing from the membrane 42, a releasable attachment means (e.g. circular area of hook-and-loop material—not shown) may be positioned to enable attachment of the acoustic sensor 40 to the ICR sensor support 20 at the specified markers 36. It is appreciated that acoustic sensors 40, applied at each site, are connected to the patient monitor leads 52 with color-coded male connector 48 that matches the corresponding female connector 52.

In one embodiment, sensor attachment to the body of the patient 10 is straightforward with assurance for both vertical and lateral position with the following steps:

(a) The upper chest strap 22 of the ICR sensor support 20 is applied and positioned immediately below the underarm locations. The strap tension is adjusted for comfort to suit the girth of the patient.

(b) The lateral position is indicated by positioning the notch 30 of the vertical separator 26 aligned with the patient sternum.

(c) The chest strap 24 of the ICR sensor support 20 is positioned with its attachment at the lower end of the vertical separator 26. The strap tension is adjusted for comfort to suit the girth of the patient.

(d) Sensor positions are then indicated via markers 36 and the acoustic sensors 40 are applied. In one embodiment, acoustic sensors 40 are applied with a simple hook-and-loop attachment between the sensor 44 housing and the corresponding hook-and-loop section 28 at each chest strap 22, 24.

(e) ECG sensors may also be added at the LA, RA, and LL standard positions indicated in FIG. 2B.

(f) The color-coded interconnect cables/leads 54 are connected at male/female connectors 48/52 to couple each sensor to a corresponding input to the patient monitor 102.

(g) Sensor 40 attachment color assignment may also be assured by the presence of keyed connectors that allow only properly assigned sensor color codes to be applied.

3. ICR System Analytics for Computing Stroke Volume

This section details methods used in data acquisition and signal processing for computing SV in accordance with the ICR monitoring system 100 of the present description. The methods detailed below are preferably implemented as instructions in machine-readable code within one or modules of application programming 110, which may be executed on monitor 102 or other external processing device.

3.1 ECG Signal Processing and Analysis

Where an ECG-gated segmentation (detailed further below) method is used, ECG signals measured using traditional ECG electrodes are used to enable timing and proper identification of phonocardiogram (PCG) acoustic signatures as belonging to S1, S2, or another part of the cardiac cycle. In each cardiac cycle, electrical depolarization of the ventricles causes a displacement in voltage observed in the ECG signal, known as the R wave. The R wave is usually the most prominent feature in the ECG signal. If the R wave can be accurately identified within each cardiac cycle, the signal can then be decomposed into individual cardiac cycles to segment the ECG signal. If the ECG and PCG are acquired synchronously, this same decomposition can be applied to the PCG. Thus, the primary objective of ECG signal processing when implemented in the methods of the present description is robust R wave detection.

R wave detection is complicated by a number of factors. First, the amplitude and morphology of the R wave can vary widely due to variations in ECG electrode placement or the presence of certain cardiac conditions. These causes also contribute to variability in the amplitude of the T wave. The T wave of the ECG reflects the electrical repolarization of the ventricles in the cardiac cycle. In some scenarios, this may result in R and T waves of similar amplitude. This creates difficulty when attempting to identify R waves based solely on amplitude criteria.

Further, several sources of noise can corrupt the ECG signal, including 1) power line interference, 2) electrode contact noise, 3) motion artifacts, 4) muscle contraction, and 5) baseline drift and amplitude modulation with respiration. Power line interference includes of 60 Hz noise that can be up to 50 percent of peak-to-peak ECG amplitude. Baseline drift and amplitude modulation often result from respiration by the subject, creating large periodic variations in the ECG baseline. Electrode contact noise is caused by degradation of coupling between the electrode and the skin. The level of noise induced is dependent upon the severity of the degradation. If there is complete loss of contact between the electrode and skin, the system is effectively disconnected, resulting in large artifacts in the ECG signal. If coupling is reduced but there is still some degree of contact between electrode and skin, a lower amplitude noise is introduced, which may persist as long as the coupling is suboptimal. Coupling issues can also be intensified by subject motion and muscle contraction, which can further affect the contact surface area between electrode and skin.

To mitigate these effects, one embodiment the ICR system 100 uses advanced preprocessing techniques, which may be implemented within application programming 110, comprising:

(a) Band-pass filtering the acquired ECG signal;
(b) Multiplication of the filtered signal by its derivative;
(c) Envelope computation;
(d) Identification of R waves in the computed envelope;
(e) Identification of corresponding peaks in the filtered signal; and
(f) Determination of R wave onset in the filtered signal.

Band pass-filtering is used to minimize the effects of baseline drift, powerline interference, and other noise sources while maintaining underlying ECG signals. A band pass filter can be defined by its lower and upper cut-off frequencies, and the region between these two frequencies is known as the pass band. While optimal cut-off frequencies may vary based on hardware, an example embodiment may have a passband between 1 Hz and 30 Hz. There exist a large number of well-defined filter design tools both for Infinite Impulse Response (IIR) and Finite Impulse Response (FIR) filters which allow for the design of bandpass filters based on desired specifications for block-band rejection, passband attenuation, filter order, and other performance specifications. In the ICR system, application of a bandpass filter can significantly improve signal to noise ratio, and subsequent preprocessing is performed on the filtered signal, f(t).

In typical ECG signals, the R wave is characterized by a large amplitude, and selection of R wave candidates based purely on amplitude can be effective. However, in some cases, T waves can become as prominent as R waves, and this straightforward approach is rendered ineffective. To mitigate the effect of elevated T waves, the ICR system exploits another characteristic of the R wave, namely it's higher frequency content relative to typical T waves. By computing the derivative of the signal f(t), an operation that amplifies high frequency content, a signal with exaggerated R wave amplitude is generated. Subsequent multiplication of f(t) with its derivative yields a new signal, g(t), that greatly emphasizes R waves relative to the sometimes-problematic T wave.

The envelope of the resulting signal, g(t), is computed using the Hilbert transform, and this envelope is subsequently low-pass filtered with a cutoff frequency of 8 Hz to further amplify the R wave, and the resulting envelope is normalized by dividing by its $98^{th}$ percentile value. Note that this approach is used rather than division by the maximum value to reduce the effects of spurious outliers in the envelope.

Peak detection of the resulting signal leverages known peak-detection algorithms with minimal peak height set to 50% of the maximum envelope height. A number of conditions can be imposed to eliminate peaks not likely to be associated with R waves. For example, excessive amplitude or an excessive number of peaks in rapid succession can be used to guide removal of false peaks prior to subsequent processing.

Once the R wave peak locations have been identified in the envelope, R wave onset is determined as the last value above a certain threshold. An example threshold here might be 50% of the envelope peak.

Figure 6A:
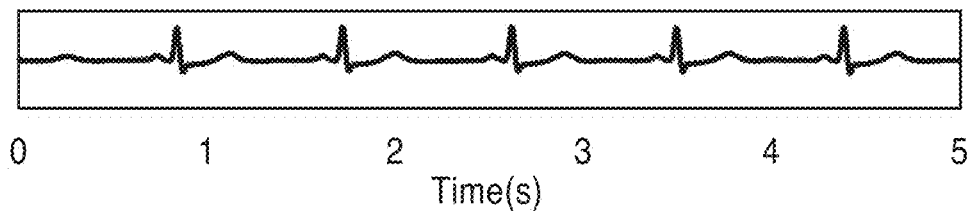
FIG. 6A through FIG. 6E show images of an exemplary PCG preprocessing and R wave detection scheme for generating a high-quality clean ECG signal.
Figure 6B:
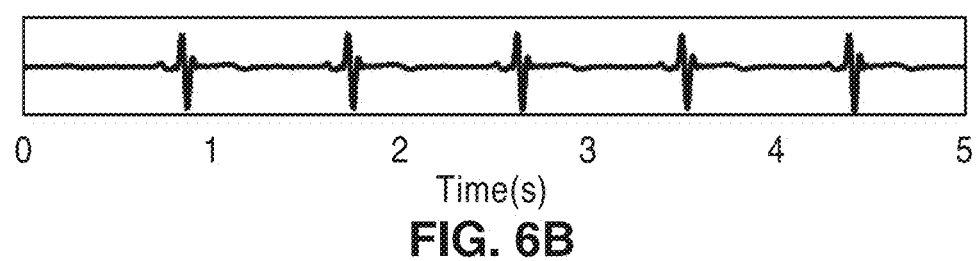
Figure 6C:
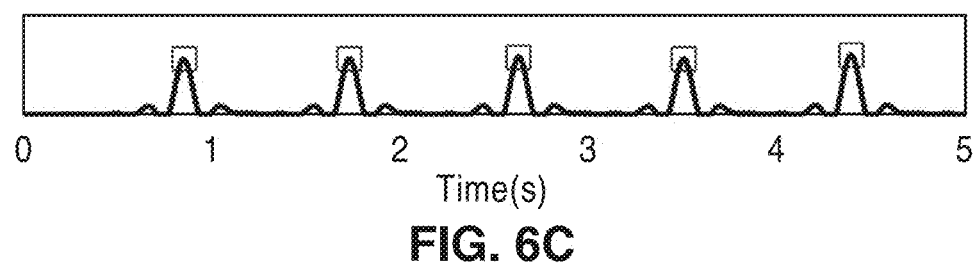
Figure 6D:
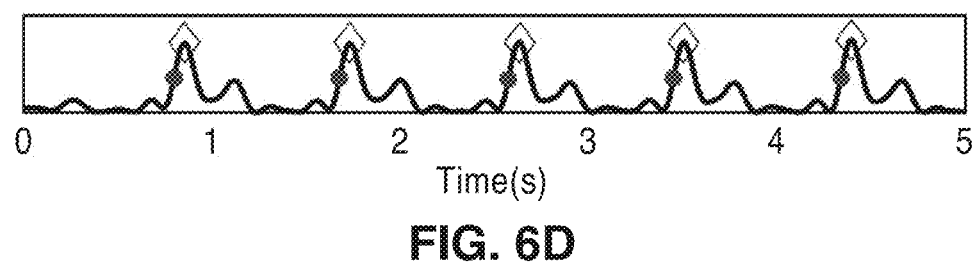
Figure 6E:
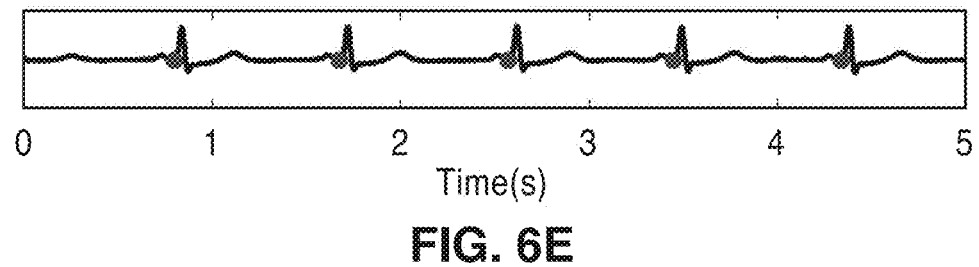

An example of PCG preprocessing and R wave detection is shown in FIG. 6A through FIG. 6E for a high-quality clean ECG signal. FIG. 6A shows the raw ECG signal. FIG. 6B shows the derivative of filtered ECG signal. FIG. 6C shows the envelope of function resulting from multiplying signal by its derivative, with detected peaks marked by squares. FIG. 6D shows the envelope of filtered signal, with detected peaks marked by diamonds, and R wave onset marked by solid circles. FIG. 6E shows the Filtered ECG signal, with R wave onset marked by solid circles.

3.2 PCG Signal Processing
3.2.1 Noise Suppression

The PCG signal is also susceptible to noise from a wide variety of sources such as involuntary subject activity, voluntary subject activity, external contact with sensor, and environmental noise.

Involuntary subject activity includes involuntary physiological activity of the subject, such as respiratory and digestive sounds. Another common noise source in this group is the microscopic movement of tissue beneath the sensor, even with a seemingly motionless subject. This motion causes persistent fluctuations in the PCG signal that are usually of relatively low amplitude. If the cardiac signal strength is low, however, this noise can mask underlying cardiac events.

Voluntary subject activity includes activity such as speech and subject motion. These noise sources will generally create large disturbances in the PCG signal. Similarly, external contact with the sensor housing by another object such as clothing or a hand can also produce large artifacts in the signal.

Environmental noise includes all external sources of noise not involving the subject or the sensor. This may include non-subject speech, background music/television, and hospital equipment noise. With proper coupling of the sensor to the tissue, such noise factors typically have minimal effect on PCG signal quality, except for in extreme cases.

PCG signal preprocessing comprises band-pass filtering followed by Short-Time Spectral Amplitude log Minimum Mean Square Error (STSA-log-MMSE) noise suppression. Band-pass filtering may be performed with cut-off frequencies of 25 and 100 Hz, which has been found to preserve PCG signals while reducing the amplitude of out-of-band noise sources.

In the method of the present description, a model of signal noise is generated, and short time segments of data are considered. A probability of the presence of acoustic activity other than noise is computed for each time segment, and a gain is computed as a function of this probability. Gain is low for low probabilities and approaches unity for high probabilities, thereby reducing the amplitude of purely noise-segments of audio. It should be noted that these models and corresponding gains are considered in the frequency domain. Conversions to frequency domain are performed using the Fast Fourier Transform (FFT), and conversions back to the temporal domain are performed using the Inverse Fast Fourier Transform (IFFT).

For PCG analysis, adaptations to the STSA-log-MMSE algorithm can be made. Whereas typical STSA-log-MMSE applications generally require a recording of known noise-only data, pre-existing knowledge of the timing of the cardiac cycle based on ECG segmentation can be leveraged to determine regions of acoustic inactivity. For example, it is known that within each cardiac cycle there will be regions that contain no cardiac sounds. Even if all cardiac sounds, including murmurs, are present, there are regions without such sounds. Thus, the regions of each cardiac cycle with RMS energy in the $25^{th}$ percentile are likely to be characterized by minimal cardiac acoustic signature. This allows for online generation of noise models and for adaptive updating of such models.

Figure 7A:
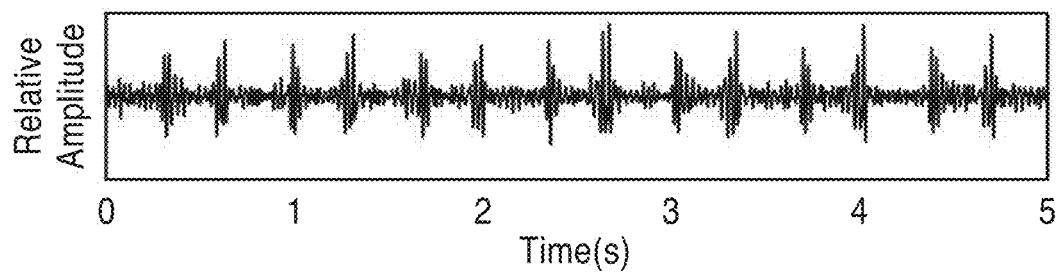
FIG. 7A through FIG. 7D illustrate an exemplary PCG signal noise suppression scheme in accordance with the present description.
Figure 7B:
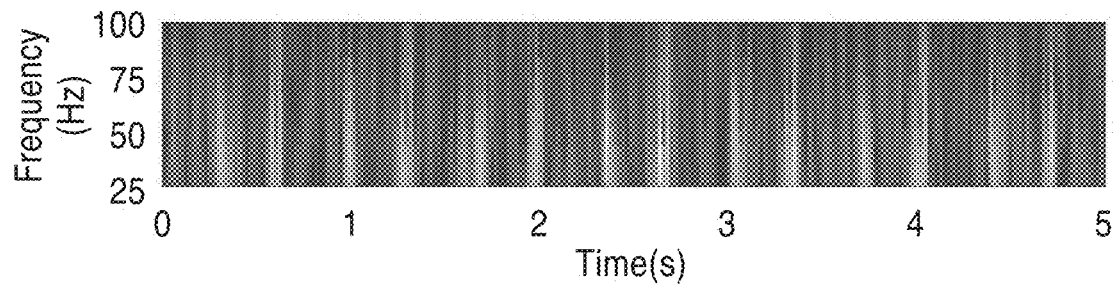
Figure 7C:
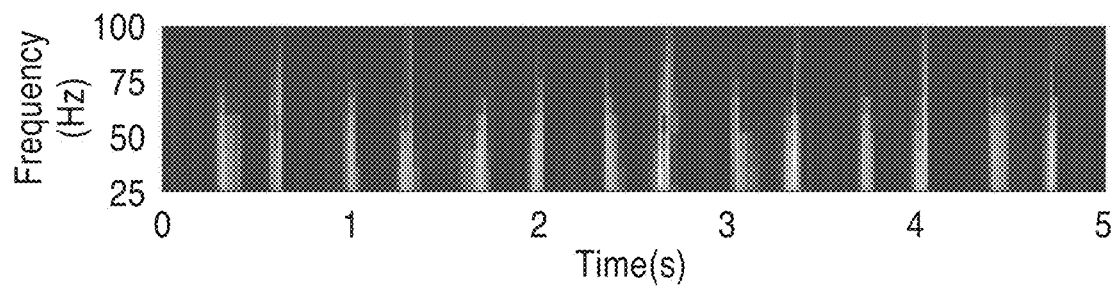
Figure 7D:
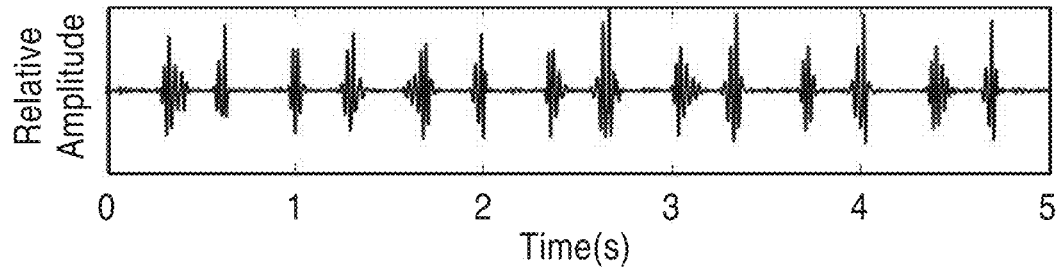

FIG. 7A through FIG. 7D illustrate an example of PCG signal noise suppression in accordance with the present description. FIG. 7A shows the original band-pass filtered signal. FIG. 7B shows a spectrogram of original signal. FIG. 7C shows a spectrogram of the de-noised or noise-suppressed signal, which demonstrates a significant reduction in noise. FIG. 7D shows the final de-noised signal, also demonstrating a significant reduction in noise.

3.3 Signal Segmentation

PCG signal analysis typically comprises three main stages:

segmentation, feature extraction, and classification/regression. In the segmentation stage, cardiac acoustic events are detected and labeled. These events may include the S1, S2, S3, and S4 sounds, as well as murmurs. Typically, the ICR system 100 leverages primarily the fundamental heart sounds, S1 and S2, as these events possess the critical information needed for our objective of estimating stroke volume (SV) via analysis of PCG signals.

The present description details two exemplary methods of PCG signal segmentation, hereinafter described as PCG-gated segmentation and ECG-gated segmentation. In PCG-gated segmentation, the PCG signal is segmented by sole examination of the PCG signal itself, without any complementary information from a synchronous ECG signal. Generally, in this approach, there is first a detection stage, in which an event detection method is applied to locate heart sounds. Here, signal processing methods are applied to emphasize regions of cardiac activity in the signal. Then, a decision method is applied to identify heart sounds based on certain predefined criteria.

Next, in the labeling stage, the sounds are labeled as one of the types described above. Quite often, this stage focuses mainly on the S1 and S2 sounds. Here, the interval duration between successive events, as well as characteristics of the events themselves, may be used to identify which group a certain event belongs to. The interval between S1 and S2 of the same cardiac cycle is the systolic interval, and the interval between S2 of one cardiac cycle and S1 of the next cardiac cycle is the diastolic interval. However, in PCG-gated segmentation, it is unknown a priori where the breakpoints of each cardiac cycle lie. Thus, when presented with two consecutive events, it can be challenging to determine whether they correspond to the S1 and S2 events of the nth cardiac cycle, or the S2 event of the nth cycle, and the S1 event of the n+1th cycle.

Finally, in the decomposition stage, the PCG signal is decomposed into individual cardiac cycles, with the corresponding events and intervals between events occurring during each cycle attributed to it. This allows for analysis of each cardiac cycle individually.

In one embodiment of the ICR system 100, an ECG-gated framework is implemented that analyzes the ECG signal, and in particular the R wave onset, to enable timing of PCG signal segmentation. This method utilizes short-time periodicity of the ECG and PCG signals, a property that exists even in cases of abnormal heart rate.

To ensure periodicity, the PCG signal is analyzed in segments containing two consecutive cardiac cycles. Assuming the systolic intervals of consecutive cardiac cycles are consistent (which we have found to be the case, even in conditions of arrhythmia), performing correlation method analysis on such a segment allows for accurate detection and labeling of S1 and S2 sounds.

The first step in PCG segmentation is the generation of PCG envelopes from the processed, noise-reduced signal described above. Envelopes may be generated using the Hilbert transform or by computing the absolute value of the signal and passing it through a low-pass filter. A number of different corner frequencies may be considered, and several envelopes may be generated and used for subsequent processing.

The envelope may be further processed by applying a threshold value to remove low-level noise. Finally, the signal may be adjusted by raising it to some power less than 1, a transform which tends to normalize the heights of peaks in the envelope such that all peaks are weighted approximately the same.

The envelopes are subsequently analyzed in segments containing two heartbeats, a preliminary segmentation that is enabled by analysis of the high-quality ECG signals generated previously. Each heartbeat is processed as the second event in one window and as the first event in the next window. As such, each cardiac cycle is analyzed twice, thereby increasing the likelihood of proper detection of that beat.

Figure 8A:
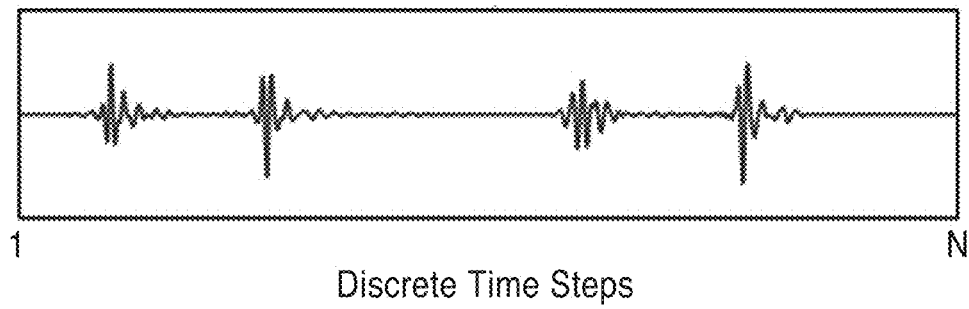
FIG. 8A through FIG. 8C show plots of the PCG signal segment, low-frequency envelope and autocorrelation of consecutive cardiac cycles, respectively.
Figure 8B:
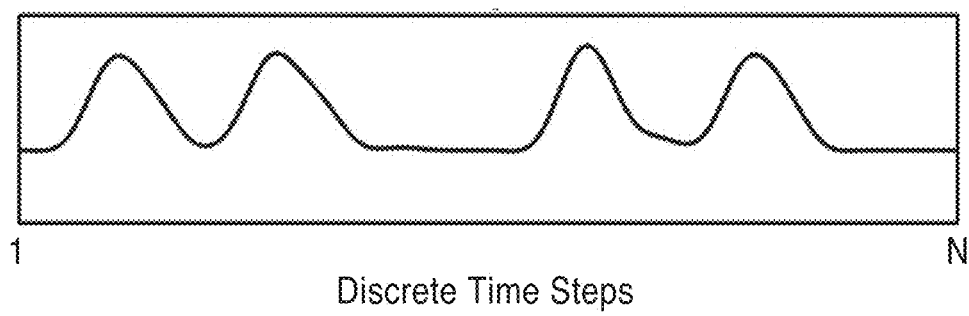
Figure 8C:
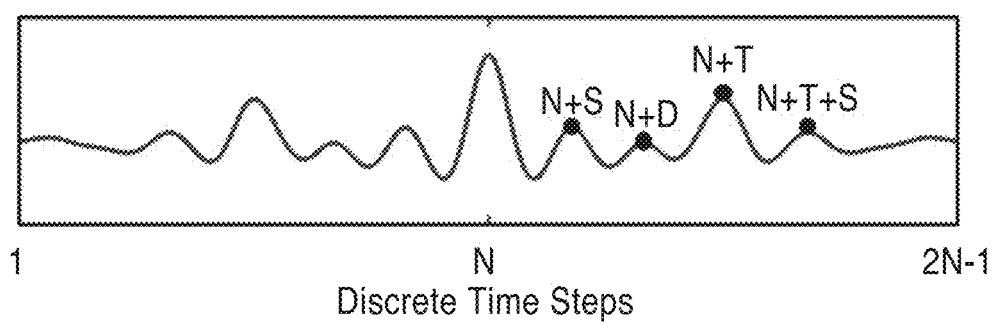

The autocorrelation function is applied to each two-beat envelope. This operator is commonly used to detect periodicity in signals, and this property is useful in PCG analysis. This process is highlighted in FIG. 8A through FIG. 8C. FIG. 8A shows a plot of the PCG signal segment of consecutive cardiac cycles. FIG. 8B shows a plot of the low-frequency envelope of corresponding segment. FIG. 8C shows a plot of the autocorrelation of low-frequency envelope. In FIG. 8C, several of the peaks are labeled by the corresponding intervals represented. It should be noted that there is a difference in scaling in the x axis between FIG. 8A through FIG. 8C.

The envelope shown in FIG. 8B is subjected to the autocorrelation operator, resulting in the symmetric signal, a(t), shown in FIG. 8C. a(t) shows a central peak, corresponding to the dot product of the envelope with itself with zero-time shift. There is also a second primary peak that is shifted by one period, T, relative to this central peak. This corresponds to the dot product of the envelope with an envelope shifted by T, such that the peaks associated with one heartbeat are aligned with those of the subsequent beat, thereby resulting in positive interference. Also evident in FIG. 8C are smaller peaks shifted by the systolic and diastolic periods, which are caused by overlap of S1 peaks with S2 peaks.

The autocorrelation described above enables computation of a valuable quality metric. For high quality PCG recordings, the peak at N+T is sharp and prominent. This prominence is quantified as the difference in its height relative to the lowest points surrounding it. This signal quality index is used to quantify signal quality, which is of critical importance in guiding subsequent algorithms. For example, if one sensor is characterized by low quality relative to others, its role in a classifier may be devalued or de-weighted relative to that of others. Alternatively, this feature can be used to alert system operators of insufficient signal quality, indicative of poor sensor placement.

Figure 9A:
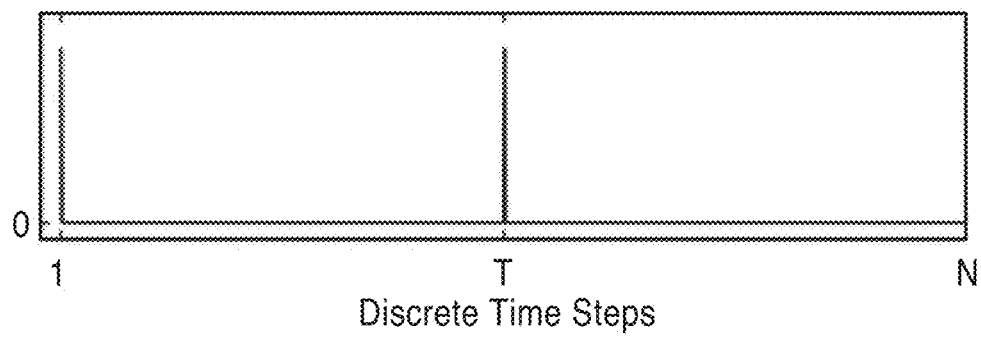
FIG. 9A through FIG. 9C show a cross-correlation method of estimating S1 locations.
Figure 9B:
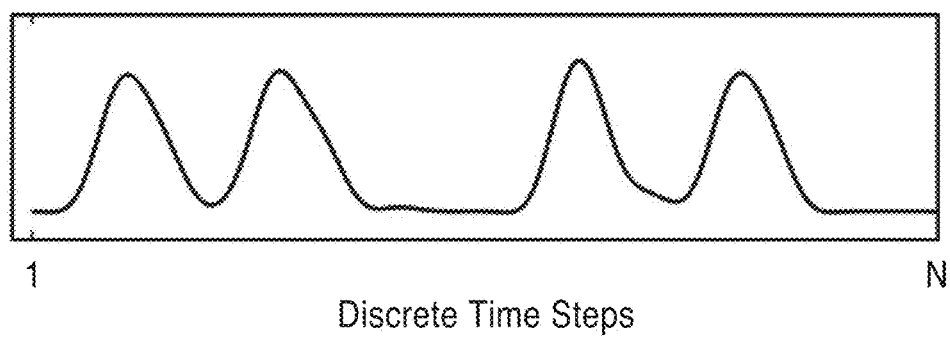
Figure 9C:
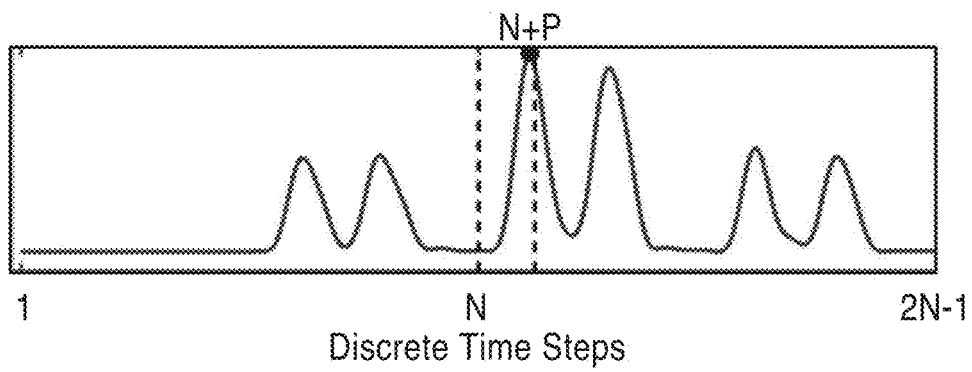

With the cardiac period, T, now determined, the next step is to determine the location of individual cardiac events within the cardiac cycle. To locate S1 events, a comb function is generated whose value is zero at all locations except at integer multiples of the period. Convolution of this function with the PCG envelope yields a series of peaks as the delta functions in the comb pass through peaks in the envelope. When these deltas align with S1 events, a large peak is generated, and the offset of this peak is equal to the offset of the S1 events in the PCG signal. This yields a search interval in the original PCG signal within which the S1 event is known to occur. This process is demonstrated in FIG. 9A through FIG. 9C, which show a cross-correlation method of estimating S1 locations. FIG. 9A shows a plot of function $f(n)$. FIG. 9B shows a plot of the low-frequency envelope of the PCG signal segment. FIG. 9C shows a plot of the cross-correlation of $f(n)$ with low-frequency envelope. In FIG. 9C, the S1 peak search interval marked with dashed lines.

Figure 10A:
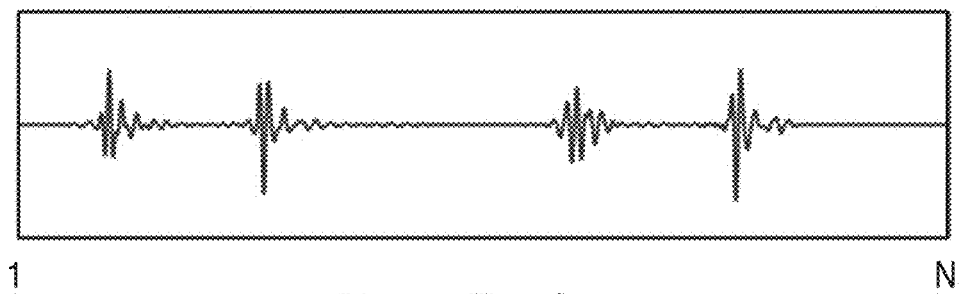
FIG. 10A through FIG. 10C show a method for autocorrelation of the high-frequency envelope segment for systolic interval estimation.
Figure 10B:
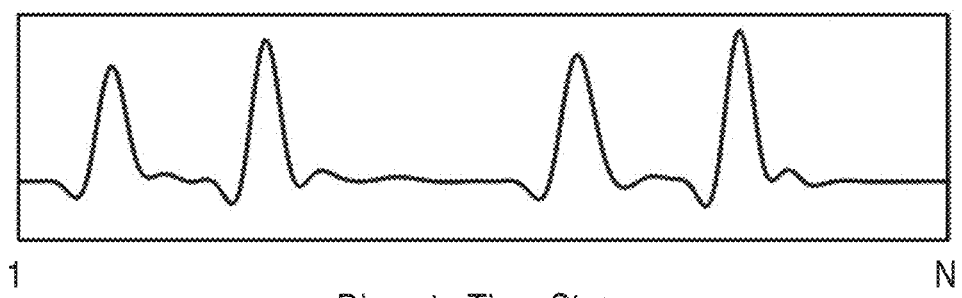
Figure 10C:
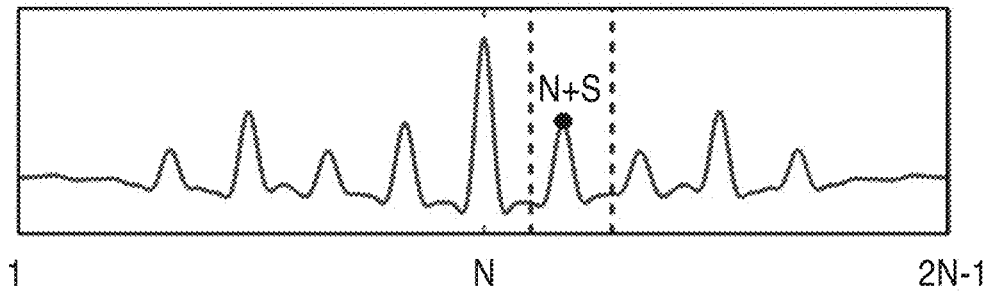

With S1 now located, the remaining task is to determine S2 location. To this end, the autocorrelation, a(t), of the PCG envelope is revisited. As described above, a(t) contains secondary peaks associated with the systolic and diastolic tie intervals. The systolic interval is given by the location of the first peak after the central peak as shown in FIG. 10A through FIG. 10C. Thus, the search region for S2 events is confined to the area around this peak. Because S2 events are not always evident in PCG signals, these peaks may not be discernible, and a search for a peak in this vicinity may yield peaks in regions where the S2 event is known not to occur. Thus, the search is limited to the region bounded by N+0.2T and N+0.55T. Peaks outside this interval are not considered. This process is demonstrated in FIG. 10A through FIG. 10C, which illustrate autocorrelation of the high-frequency envelope segment for systolic interval estimation. FIG. 10A shows a plot of the PCG signal segment. FIG. 10B shows a plot of the high-frequency envelope. FIG. 10C shows the resulting autocorrelation of the high-frequency envelope. In FIG. 10C, the dashed lines represent boundaries of $N+0.2T<n<N+0.55T$.

As a final step in PCG signal segmentation, false event removal methods may be applied. This may leverage timing and duration properties, as well as other known signal characteristics. For example, the time interval between onset of the R wave and onset of the S1 sounds is typically very consistent, a property than can be leveraged to remove detected S1 peaks that occur significantly before or after the expected time.

Additionally, cardiac events are characterized by durations of 20 ms to 250 ms. If a detected peak has a duration outside of this range, it is likely an artifact of noise and can be removed from consideration.

3.4 PCG Features and Feature Extraction

In a preferred embodiment of the ICR monitoring system 100, the systems and methods may be optimized to utilize extensive studies performed on healthy and afflicted individuals features shown to correlate with SV. Features quantifying temporal and signal amplitude characteristics have previously been combined with frequency analysis to compute critical cardiac values, such as, but not limited to, Ejection Fraction (EF). Since EF is closely related to SV, computed EF may be used as an input for subsequent SV classification. Further, a novel frequency analysis method known as Phonogram Carrier Signal Analysis (PCSA) enables computation of features correlating strongly with SV. These PCSA-based features are also used as inputs.

3.4.1 Computed Ejection Fraction

Description of the methods used to compute EF from ECG and PCG signals may be found with reference to U.S. Application No. PCT/US2018/046378, filed on Aug. 10, 2018, incorporated herein by reference in its entirety. In short, a number of features relating to temporal and amplitude characteristics are extracted from PCG signals. Further, PCSA methods may be used to generate additional features. A Neural Network (NN) approach may be used to compute EF values across all subjects to generate a "global classifier." Subjects may be assigned to a set of subgroups based on this computed value, where each such subgroup has its own NN sub-classifier, which may be used to compute final EF values. This type of approach is known as a tiered NN classifier.

3.4.2 Frequency Characteristics

Figure 11A:
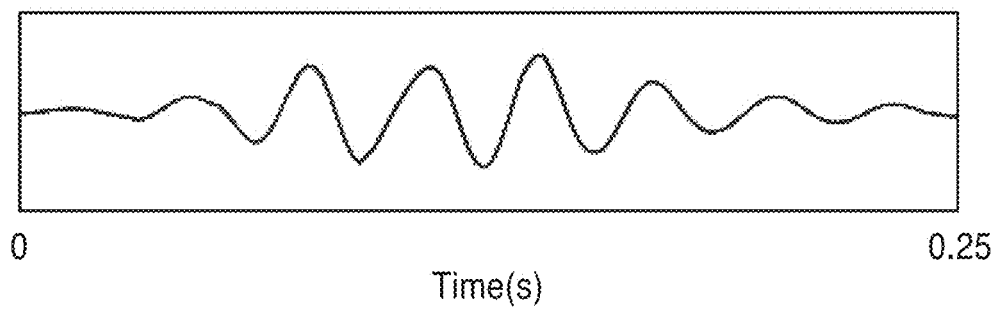
FIG. 11A through FIG. 11C illustrate a method for AM-FM decomposition of an S1 event.
Figure 11B:
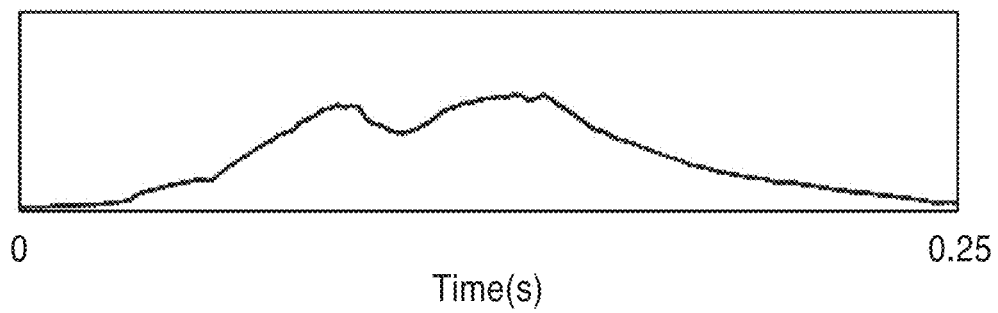
Figure 11C:
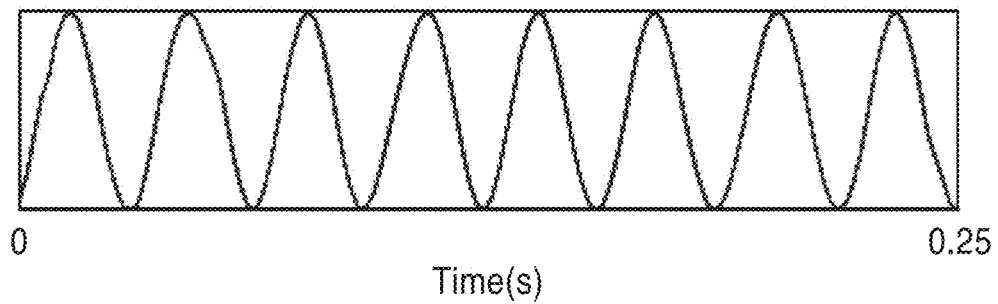

The frequency domain has been found to yield further sets of valuable features. In particular, an AM-FM decomposition of S1 and S2 sounds was found to provide a powerful dimension-reduction capability and to enable discovery of new features correlating strongly with SV. FIG. 11A through FIG. 11C illustrate a method for AM-FM decomposition of an S1 event. FIG. 11A shows a plot of the PCG signal segment of S1 event. FIG. 11B shows a plot of the AM component. FIG. 11C shows a plot of the FM component (carrier signal).

In an AM-FM decomposition, a PCG signal is represented as an envelope b(t) multiplied by a carrier signal, f(t), which is defined as having unit amplitude. By dividing the original signal by a model of b(t), a carrier signal with unit amplitude is recovered, and the FFT of this signal yields its frequency content. This process, defined as Phonocardiogram Carrier Signal Analysis (PCSA), has been found to yield features strongly correlated with SV.

For example, one valuable feature has been defined as the ratio between the energy content contained in a high-frequency band of f(t) relative to that contained in a low-frequency band. The energy associated with a band is computed as the sum of the FFT of f(t) with limits provided by the upper and lower limits of the band. For example, a band might be defined by lower and upper limits of 10 Hz and 15 Hz respectively, and the energy contained in this band would be computed as the sum of the FFT from 10 Hz to 15 Hz. By defining a low and a high frequency band, computing the associated energy for each band, and then computing the ratio, $R_{PCSA}$, of these energies, a powerful PCSA feature can be computed.

3.5 Optimization of PCSA Frequency Ratios

The computed quantity, $R_{PCSA}$, is parameterized by four values, namely the lower and upper limits of the lower and upper frequency bands. In order to optimize this computed value for subsequent SV computation, these four values are selected based on training data. To this end, the Pearson Correlation Coefficient (PCC) as well as the linear regression correlation coefficient are considered. These two values quantify the extent to which an input variable (in this case, $R_{PCSA}$) correlates with an output variable (in this case, SV). A zero value indicates zero correlation, and an absolute value of one indicates perfect correlation. Thus, selection of optimal parameters in computing $R_{PCSA}$ is equivalent to maximizing the correlation coefficient between $R_{PCSA}$ and SV with these four frequency values as inputs. Constraints may be placed on the frequency bands to reduce the size of the four-dimensional search space. For example, the upper limit of a frequency band must be larger than its lower limit. Further, the lower limit of the high frequency band must be above the upper limit of the low frequency band.

A number of methods can be used to perform this optimization. A brute force method can be used that considers all possible combinations of frequency bands, computes the result correlation coefficient for each combination, and records the maximum such coefficient. Alternatively, a constrained non-convex optimization routine may be executed a large number of times with randomly selected initial seeds, each time converging to a local maximum. The largest such local optimum would be considered the best solution. Finally, a lower dimensional search space may be considered by, for example, constraining the width of the upper and lower bands and only varying their respective center frequencies. The resulting two-dimensional optimization can be performed much faster at the cost of potentially overlooking optimal solutions. Any of the above methods can be computed more rapidly via a highly parallelized computing structure such as a cluster or network of computing machines.

3.6 Stroke Volume from Computed EF and PCSA

Figure 12:
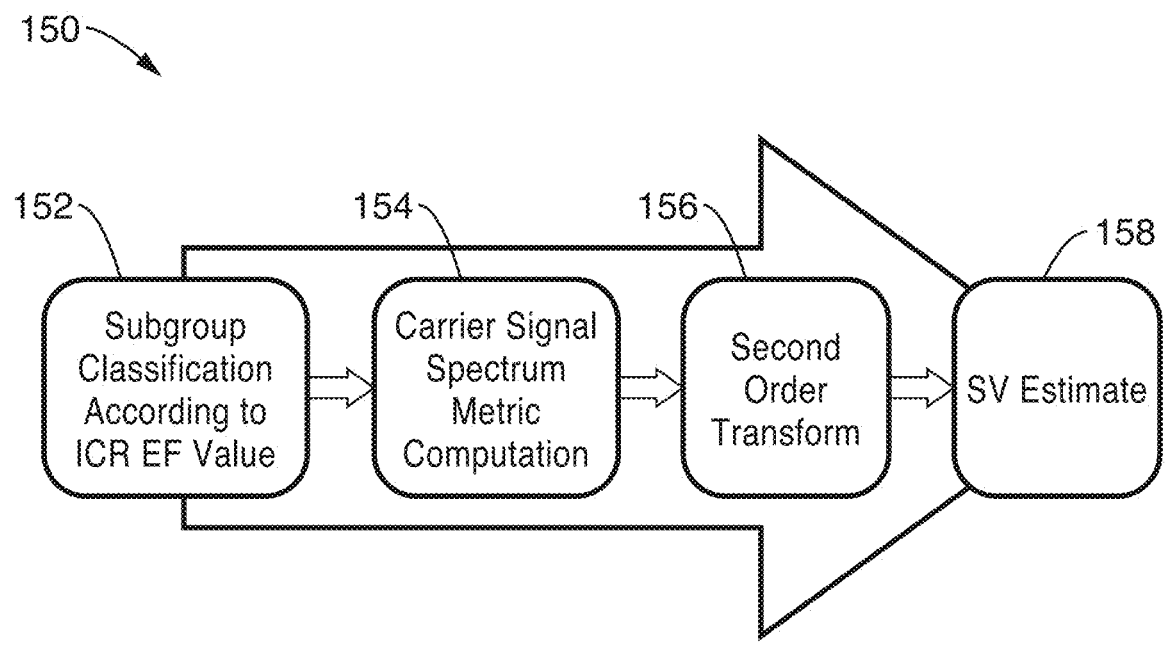
FIG. 12 shows a schematic flow diagram of an exemplary SV computation process 150 in accordance with the present description.

FIG. 12 shows a schematic flow diagram of an exemplary SV computation process 150 using both EF and PCSA as inputs in accordance with the present description. To compute SV, subjects are first assigned into subgroups at step 152 based on computed EF values. Next, at step 154, the carrier signal spectrum metric the PCSA feature value, $R_{PCSA}$, is computed. Within each such subgroup, a second order quadratic transform is applied at step 156 to the PCSA values to compute an SV estimate 158. Each subgroup has its own quadratic transform, which is generated based on training data. This process is performed for both S1 and S2 events, and the global SV value is computed as the average of these two values.

Figure 13:
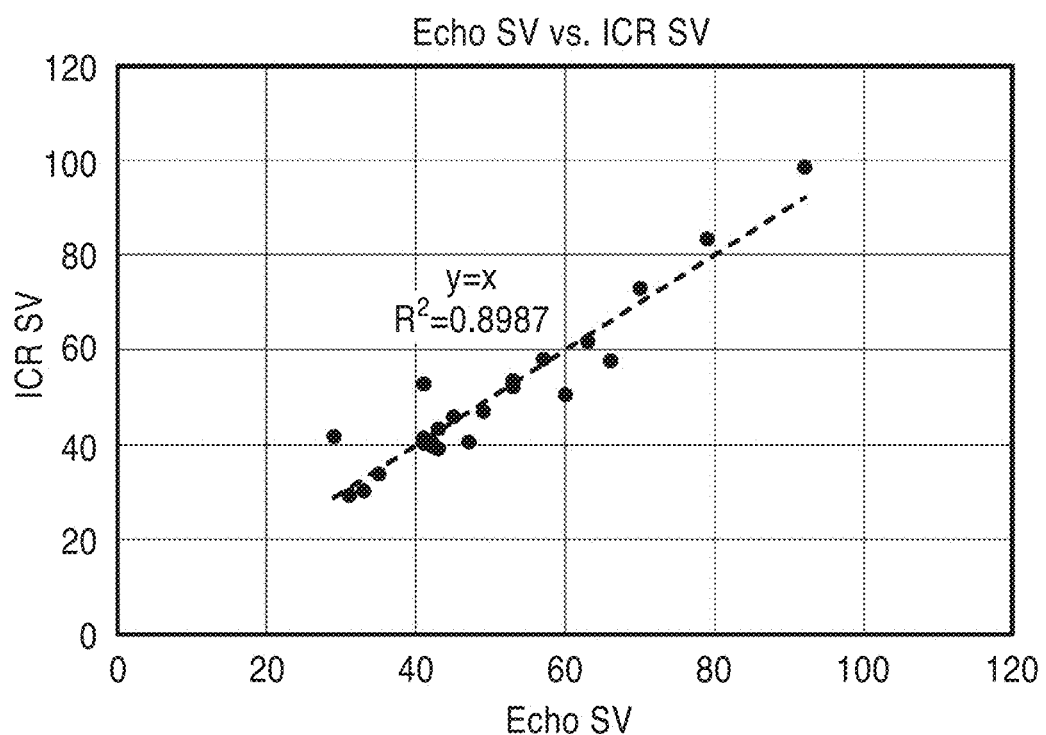
FIG. 13 shows a plot of results of the global SV classifier for an exemplary set of subjects.

FIG. 13 shows a plot of results of the global SV classifier for an exemplary set of subjects. Computed SV values are plotted against SV as measured using echocardiography. It is clear that the global SV classifier accurately computes SV.

After the SV global classifier is applied, subjects are assigned to subgroups based on this computed SV value. Final SV is computed within each group using a second order transform. As before, each subgroup has its own second order transform. Further, the process is performed for both S1 and S2 data, and the final SV value is computed as the average of these two values.

3.7 Stroke Volume Computed via Neural Network

In addition to, or as an alternative to the quadratic transform method described above, a Neural Network (NN) approach may be employed to compute SV. In this approach, one or more of computed EF, Temporal and Amplitude features, and PCSA features are used as inputs to a neural network. A single NN classifier may be used, or alternatively a tiered approach is used in which an initial global NN is used to assign subjects into subgroups, and then subjects within each subgroup are further classified using a secondary NN.

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general-purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure (s) algorithm(s), step(s), operation(s), form ula(e), or computational depiction(s).

It will further be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors.

It will further be appreciated that as used herein, that the terms processor, hardware processor, computer processor, central processing unit (CPU), and computer are used synonymously to denote a device capable of executing the instructions and communicating with input/output interfaces and/or peripheral devices, and that the terms processor, hardware processor, computer processor, CPU, and computer are intended to encompass single or multiple devices, single core and multicore devices, and variations thereof.

From the description herein, it will be appreciated that that the present disclosure encompasses multiple embodiments which include, but are not limited to, the following:

1. An apparatus for monitoring cardiac stroke volume (SV) in a patient, the apparatus comprising: (a) a plurality of Integrated Cardio Respiratory (ICR) acoustic sensors configured to be positioned on the chest of the patient; (b) a processor coupled to the plurality of ICR acoustic sensors; and (c) a non-transitory memory storing instructions executable by the processor; (d) wherein said instructions, when executed by the processor, perform steps comprising: (i) receiving a phonocardiogram (PCG) acoustic signal from the plurality of ICR acoustic sensors; (ii) segmenting the PCG acoustic signal to locate one or more cardiac events in the PCG acoustic signal; (iii) extracting one or more of temporal and amplitude characteristics from the PCG acoustic signal; (iv) classifying the extracted characteristics into one or more subgroups; (v) computing a SV of the patient based on the classified characteristics; and (vi) outputting the computed SV of the patient.

2. The method or apparatus of any preceding or following embodiment, wherein computing a SV of the patient comprises: computing ejection fraction (EF) vales based on the extracted characteristics; assigning a subject into a subgroup based on computed EF values; computing a carrier signal via PCSA; and within each such subgroup, applying a second order quadratic transform to compute an SV estimate.

3. The method or apparatus of any preceding or following embodiment, wherein each quadratic transform is generated using training data.

4. The method or apparatus of any preceding or following embodiment: wherein the quadratic transform is applied to both S1 and S2 events extracted from the PCG data; and wherein a global SV value is computed as an average of values of the transform of the S1 and S2 events.

5. The method or apparatus of any preceding or following embodiment, wherein segmenting the PCG acoustic signal comprises: detecting heart sounds within the PCG acoustic signal; identifying the heart sounds based on predefined criteria; labeling heart sounds as S1 and S2 based on an interval between successive events; and decomposing the PCG signal into individual cardiac cycles.

6. The method or apparatus of any preceding or following embodiment, further comprising: (e) a plurality of ECG sensors configured to be positioned on the chest of a patient and coupled to the processor; (f) wherein said instructions, when executed by the processor, further perform steps comprising: (i) receiving an ECG sensor signal from the plurality of ECG sensors; (ii) processing the ECG sensor signal to calculate an R wave onset in the ECG sensor signal; (iii) wherein the R wave onset is used enable timing and identification of PCG acoustic signatures within the cardiac cycle.

7. The method or apparatus of any preceding or following embodiment, wherein identification of PCG acoustic signatures comprises identification of S1 and S2 events within the cardiac cycle.

8. The method or apparatus of any preceding or following embodiment, wherein the extracted temporal characteristics comprise one or more of: electromechanical activation time (EMAT), total electromechanical systolic interval ($QS_2$), S1 duration, S2 duration, mitral cessation-to-opening time (MCOT), left ventricular ejection time (LVET), and left-ventricular systolic time (LVST).

9. The method or apparatus of any preceding or following embodiment: wherein the PCG signal is analyzed in within an envelope segment containing two consecutive cardiac cycles; and wherein the extracted amplitude characteristics comprise one or more of: the root-mean-square (RMS) of the PCG signal envelope segment normalized by RMS of the PCG signal of the entire cardiac cycle; the peak amplitude of the PCG signal segment, normalized by variance of the PCG signal of the entire cardiac cycle; and the peak amplitude of envelope segment, normalized by the envelope mean value for the entire cardiac cycle.

10. The method or apparatus of any preceding or following embodiment, further comprising: extracting one or more frequency characteristics from the PCG signal by performing Phonocardiogram Carrier Signal Analysis (PCSA).

11. The method or apparatus of any preceding or following embodiment, wherein PCSA comprises AM-FM decomposition of S1 and S2 events within the PCG signal to yield a carrier signal with unit amplitude.

12. The method or apparatus of any preceding or following embodiment, wherein processing the ECG sensor signal to calculate an R wave onset in the signal comprises: band-pass filtering the ECG sensor signal; multiplying the filtered signal by its derivative; computing an envelope of the multiplied signal; identifying R waves in the computed envelope; identifying corresponding peaks in the filtered signal; and determining an R wave onset in filtered signal.

13. The method or apparatus of any preceding or following embodiment, wherein classifying the extracted characteristics comprises applying a Neural Network (NN) across a plurality of patients to generate a global classifier, and assigning patients to a set of subgroups based on a computed SV value, where each such subgroup has its own NN sub-classifier.

14. The method or apparatus of any preceding or following embodiment, wherein the plurality of ICR acoustic sensors disposed within an ICR sensor support configured to support the ICR acoustic sensors on the patient at locations based on typical auscultatory sites.

15. The method or apparatus of any preceding or following embodiment, wherein said instructions, when executed by the processor, perform steps further comprising: preprocessing the PCG acoustic signal using Short-Time Spectral Amplitude Log Minimum Mean Square Error (STSA-log-MMSE) noise suppression; and wherein timing of the cardiac cycle based the acquired R wave onset is used to determine regions of acoustic inactivity as an input to STSA-log-MMSE.

16. A method for monitoring cardiac stroke volume (SV) within a patient, the method comprising: receiving a phonocardiogram (PCG) acoustic signal from the plurality of ICR acoustic sensors positioned on the chest of a patient; segmenting the PCG acoustic signal to locate one or more cardiac events in the PCG acoustic signal; extracting one or more of temporal and amplitude characteristics from the PCG acoustic signal; classifying the extracted characteristics into one or more subgroups; computing a SV of the patient based on the classified characteristics; and outputting the computed SV of the patient for display; wherein said method is performed by a processor executing instructions stored on a non-transitory memory.

17. The method or apparatus of any preceding or following embodiment, wherein computing a SV of the patient comprises: computing ejection fraction (EF) vales based on the extracted characteristics; assigning a subject into a subgroup based on computed EF values; computing a carrier signal via PCSA; and within each such subgroup, applying a second order quadratic transform to compute an SV estimate.

18. The method or apparatus of any preceding or following embodiment, wherein each quadratic transform is generated using training data.

19. The method or apparatus of any preceding or following embodiment: wherein the quadratic transform is applied to both S1 and S2 events extracted from the PCG data; and wherein a global SV value is computed as an average of values of the transform of the S1 and S2 events.

20. The method or apparatus of any preceding or following embodiment, wherein segmenting the PCG acoustic signal comprises: detecting heart sounds within the PCG acoustic signal; identifying the heart sounds based on predefined criteria; labeling heart sounds as S1 and S2 based on an interval between successive events; and decomposing the PCG signal into individual cardiac cycles.

21. The method or apparatus of any preceding or following embodiment, further comprising: receiving an ECG sensor signal, concurrently with reception of the PCG acoustic signal, from the plurality of ECG sensors positioned on the chest of the patient processing the ECG sensor signal to calculate an R wave onset in the ECG sensor signal; and wherein the R wave onset is used enable timing and identification of PCG acoustic signatures within the cardiac cycle.

22. The method or apparatus of any preceding or following embodiment, wherein identification of PCG acoustic signatures comprises identification of S1 and S2 events within the cardiac cycle.

23. The method or apparatus of any preceding or following embodiment, wherein the extracted temporal characteristics comprise one or more of: electromechanical activation time (EMAT), total electromechanical systolic interval ($QS_2$), S1 duration, S2 duration, mitral cessation-to-opening time (MCOT), left ventricular ejection time (LVET), and left-ventricular systolic time (LVST).

24. The method or apparatus of any preceding or following embodiment: wherein the PCG signal is analyzed in within an envelope segment containing two consecutive cardiac cycles; and wherein the extracted amplitude characteristics comprise one or more of: the root-mean-square (RMS) of the PCG signal envelope segment normalized by RMS of the PCG signal of the entire cardiac cycle; the peak amplitude of the PCG signal segment, normalized by variance of the PCG signal of the entire cardiac cycle; and the peak amplitude of envelope segment, normalized by the envelope mean value for the entire cardiac cycle.

25. The method or apparatus of any preceding or following embodiment, further comprising: extracting one or more frequency characteristics from the PCG signal by performing Phonocardiogram Carrier Signal Analysis (PCSA).

26. The method or apparatus of any preceding or following embodiment, wherein PCSA comprises AM-FM decomposition of S1 and S2 events within the PCG signal to yield a carrier signal with unit amplitude.

27. The method or apparatus of any preceding or following embodiment, wherein processing the ECG sensor signal to calculate an R wave onset in the signal comprises: band-pass filtering the ECG sensor signal; multiplying the filtered signal by its derivative; computing an envelope of the multiplied signal; identifying R waves in the computed envelope; identifying corresponding peaks in the filtered signal; and determining an R wave onset in filtered signal.

28. The method or apparatus of any preceding or following embodiment, wherein classifying the extracted characteristics comprises applying a Neural Network (NN) across a plurality of patients to generate a global classifier, and assigning patients to a set of subgroups based on a computed SV value, where each such subgroup has its own NN sub-classifier.

29. The method or apparatus of any preceding or following embodiment, wherein said instructions, when executed by the processor, perform steps further comprising: preprocessing the PCG acoustic signal using Short-Time Spectral Amplitude Log Minimum Mean Square Error (STSA-log-MMSE) noise suppression; and wherein timing of the cardiac cycle based the acquired R wave onset is used to determine regions of acoustic inactivity as an input to STSA-log-MMSE.

30. An apparatus for monitoring cardiac stroke volume, the apparatus comprising: (a) a plurality of ECG sensors configured to be positioned on the chest of a patient; (b) a plurality of Integrated CardioRespiratory (ICR) acoustic sensors configured to be positioned on the chest of a patient; (c) a processor coupled to the plurality of ECG sensors and ICR acoustic sensors; and (d) a non-transitory memory storing instructions executable by the processor; (e) wherein said instructions, when executed by the processor, perform steps comprising: (i) receiving a signal from the plurality of ECG sensors; (ii) band-pass filtering the signal; (iii) multiplying the filtered signal by its derivative; (iv) computing an envelope of the multiplied signal; (v) identifying R waves in the computed envelope; (vi) identifying corresponding peaks in the filtered signal; and (vii) determining an R wave onset in filtered signal.

31. The method or apparatus of any preceding or following embodiment, wherein said instructions further perform steps comprising: (viii) receiving a phonocardiogram (PCG) acoustic signal from the ICR acoustic sensors; (ix) computing ejection fraction (EF); (x) computing Phonocardiogram Carrier Signal Analysis (PCSA); and (xi) computing stoke volume from the computed EF and PCSA.

32. A method for monitoring cardiac stroke volume, the method comprising: (a) receiving a signal from a plurality of ECG sensors; (b) band-pass filtering the signal; (c) multiplying the filtered signal by its derivative; (d) computing an envelope of the multiplied signal; (e) identifying R waves in the computed envelope; (f) identifying corresponding peaks in the filtered signal; and (g) determining an R wave onset in filtered signal; (h) wherein said method is performed by a processor executing instructions stored on a non-transitory memory.

33. The method or apparatus of any preceding or following embodiment, further comprising the steps of: (i) receiving a phonocardiogram (PCG) acoustic signal from a plurality of ICR acoustic sensors; (j) computing ejection fraction (EF); (k) computing Phonocardiogram Carrier Signal Analysis (PCSA); and (l) computing stoke volume from the computed EF and PCSA.

As used herein, the singular terms "a," "an," and "the" may include plural referents unless the context clearly dictates otherwise. Reference to an object in the singular is not intended to mean "one and only one" unless explicitly so stated, but rather "one or more."

As used herein, the term "set" refers to a collection of one or more objects. Thus, for example, a set of objects can include a single object or multiple objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

Sensor Application System Size Ranges According To Patient Height

| ICR Sensor Application System Size | Patient Height (inches) | Patient Height (cm) |
| --- | --- | --- |
| X-Small | (less than 66) | (less than 168) |
| Small | (66-68) | (168-173) |
| Medium | (68-71) | (173-180) |
| Large | (71-74) | (180-188) |
| X_Large | (greater than 74) | (greater than 188) |

What is claimed is:

1. An apparatus for monitoring cardiac stroke volume (SV) in a patient, the apparatus comprising:
   (a) a plurality of Integrated Cardio Respiratory (ICR) acoustic sensors configured to be positioned on the chest of the patient;
   (b) a processor coupled to the plurality of ICR acoustic sensors; and
   (c) a non-transitory memory storing instructions executable by the processor;
   (d) wherein said instructions, when executed by the processor, perform steps comprising:
      (i) receiving a phonocardiogram (PCG) acoustic signal from the plurality of ICR acoustic sensors;
      (ii) segmenting the PCG acoustic signal to locate one or more cardiac events in the PCG acoustic signal;
      (iii) extracting one or more of temporal and amplitude characteristics from the PCG acoustic signal;
      (iv) classifying the extracted characteristics into one or more subgroups;
      (v) computing the SV of the patient based on the classified characteristics; and
      (vi) outputting the computed SV of the patient.

2. The apparatus of claim 1, wherein computing a SV of the patient comprises:
   computing ejection fraction (EF) values based on the extracted characteristics;
   assigning a subject into a subgroup based on computed EF values;
   computing a carrier signal from calculated RPCSA values of the PCG acoustical signals; and
   within each such subgroup, applying a second order quadratic transform to compute an SV estimate.

3. The apparatus of claim 2, wherein each quadratic transform is generated using training data.

4. The apparatus of claim 3:
   wherein the quadratic transform is applied to both S1 and S2 events extracted from the PCG data; and
   wherein a global SV value is computed as an average of values of the transform of the S1 and S2 events.

5. The apparatus of claim 1, wherein segmenting the PCG acoustic signal comprises:
   detecting heart sounds within the PCG acoustic signal;
   identifying the heart sounds based on predefined criteria;
   labeling heart sounds as S1 and S2 based on an interval between successive events; and
   decomposing the PCG signal into individual cardiac cycles.

6. The apparatus of claim 1, further comprising:
   (e) a plurality of ECG sensors configured to be positioned on the chest of a patient and coupled to the processor;
   (f) wherein said instructions, when executed by the processor, further perform steps comprising:
      (i) receiving an ECG sensor signal from the plurality of ECG sensors;
      (ii) processing the ECG sensor signal to calculate an R wave onset in the ECG sensor signal;
      (iii) wherein the R wave onset is used enable timing and identification of PCG acoustic signatures within the cardiac cycle.

7. The apparatus of claim 6, wherein the identification of PCG acoustic signatures comprises identification of S1 and S2 events within the cardiac cycle.

8. The apparatus of claim 7, wherein the extracted temporal characteristics comprise one or more of:
   electromechanical activation time (EMAT), total electromechanical systolic interval ($QS_2$), S1 duration, S2 duration, mitral cessation-to-opening time (MCOT), left ventricular ejection time (LVET), and left-ventricular systolic time (LVST).

9. The apparatus of claim 7:
   wherein the PCG signal is analyzed in within an envelope segment containing two consecutive cardiac cycles; and
   wherein the extracted amplitude characteristics comprise one or more of: the root-mean-square (RMS) of the PCG signal envelope segment normalized by RMS of the PCG signal of the entire cardiac cycle; the peak amplitude of the PCG signal segment, normalized by variance of the PCG signal of the entire cardiac cycle; and the peak amplitude of envelope segment, normalized by the envelope mean value for the entire cardiac cycle.

10. The apparatus of claim 1, further comprising:
    extracting one or more frequency characteristics from the PCG signal by performing Phonocardiogram Carrier Signal Analysis (PCSA).

11. The apparatus of claim 10, wherein PCSA comprises AM-FM decomposition of S1 and S2 events within the PCG signal to yield a carrier signal with unit amplitude.

12. The apparatus of claim 6, wherein processing the ECG sensor signal to calculate an R wave onset in the signal comprises:
    band-pass filtering the ECG sensor signal;
    multiplying the filtered signal by its derivative;
    computing an envelope of the multiplied signal;
    identifying R waves in the computed envelope;
    identifying corresponding peaks in the filtered signal; and
    determining an R wave onset in filtered signal.

13. The apparatus of claim 1, wherein classifying the extracted characteristics comprises applying a Neural Network (NN) across a plurality of patients to generate a global classifier, and assigning patients to a set of subgroups based on a computed SV value, where each such subgroup has its own NN sub-classifier.

14. The apparatus of claim 1, wherein the plurality of ICR acoustic sensors disposed within an ICR sensor support configured to support the ICR acoustic sensors on the patient at locations based on typical auscultatory sites.

15. The apparatus of claim 1, wherein said instructions, when executed by the processor, perform steps further comprising:
    preprocessing the PCG acoustic signal using Short-Time Spectral Amplitude Log Minimum Mean Square Error (STSA-log-MMSE) noise suppression; and
    wherein timing of the cardiac cycle based the acquired R wave onset is used to determine regions of acoustic inactivity as an input to STSA-log-MMSE.

16. A method for monitoring cardiac stroke volume (SV) within a patient, the method comprising:

receiving a phonocardiogram (PCG) acoustic signal from the plurality of ICR acoustic sensors positioned on the chest of a patient;

segmenting the PCG acoustic signal to locate one or more cardiac events in the PCG acoustic signal;

extracting one or more of temporal and amplitude characteristics from the PCG acoustic signal;

classifying the extracted characteristics into one or more subgroups;

computing the SV of the patient based on the classified characteristics; and outputting the computed SV of the patient for display;

wherein said method is performed by a processor executing instructions stored on a non-transitory memory.

17. The method of claim 16, wherein computing a the SV of the patient comprises:

computing ejection fraction (EF) values based on the extracted characteristics;

assigning a subject into a subgroup based on computed EF values;

computing a carrier signal from calculated RPCSA values of the PCG acoustical signals; and within each such subgroup, applying a second order quadratic transform to compute an SV estimate.

18. The method of claim 17, wherein each quadratic transform is generated using training data.

19. The method of claim 18:

wherein the quadratic transform is applied to both S1 and S2 events extracted from the PCG data; and wherein a global SV value is computed as an average of values of the transform of the S1 and S2 events.

20. The method of claim 19, wherein segmenting the PCG acoustic signal comprises:

detecting heart sounds within the PCG acoustic signal;

identifying the heart sounds based on predefined criteria;

labeling heart sounds as S1 and S2 based on an interval between successive events; and decomposing the PCG signal into individual cardiac cycles.

21. The method of claim 19, further comprising:

receiving an ECG sensor signal, concurrently with reception of the PCG acoustic signal, from the plurality of ECG sensors positioned on the chest of the patient processing the ECG sensor signal to calculate an R wave onset in the ECG sensor signal; and wherein the R wave onset is used enable timing and identification of PCG acoustic signatures within the cardiac cycle.

22. The method of claim 21, wherein identification of PCG acoustic signatures comprises identification of S1 and S2 events within the cardiac cycle.

23. The method of claim 22, wherein the extracted temporal characteristics comprise one or more of:

electromechanical activation time (EMAT), total electromechanical systolic interval ($QS_2$), S1 duration, S2 duration, mitral cessation-to-opening time (MCOT), left ventricular ejection time (LVET), and left-ventricular systolic time (LVST).

24. The method of claim 22:

wherein the PCG signal is analyzed in an envelope segment containing two consecutive cardiac cycles; and wherein the extracted amplitude characteristics comprise one or more of: the root-mean-square (RMS) of the PCG signal envelope segment normalized by RMS of the PCG signal of the entire cardiac cycle; the peak amplitude of the PCG signal segment, normalized by variance of the PCG signal of the entire cardiac cycle; and the peak amplitude of envelope segment, normalized by the envelope mean value for the entire cardiac cycle.

25. The method of claim 19, further comprising:

extracting one or more frequency characteristics from the PCG signal by performing Phonocardiogram Carrier Signal Analysis (PCSA).

26. The method of claim 25, wherein PCSA comprises AM-FM decomposition of S1 and S2 events within the PCG signal to yield a carrier signal with unit amplitude.

27. The method of claim 25, wherein processing the ECG sensor signal to calculate an R wave onset in the signal comprises:

band-pass filtering the ECG sensor signal;

multiplying the filtered signal by its derivative;

computing an envelope of the multiplied signal;

identifying R waves in the computed envelope;

identifying corresponding peaks in the filtered signal; and determining an R wave onset in filtered signal.

28. The method of claim 19, wherein classifying the extracted characteristics comprises applying a Neural Network (NN) across a plurality of patients to generate a global classifier, and assigning patients to a set of subgroups based on a computed SV value, where each such subgroup has its own NN sub-classifier.

29. The method of claim 19, wherein said instructions, when executed by the processor, perform steps further comprising:

preprocessing the PCG acoustic signal using Short-Time Spectral Amplitude Log Minimum Mean Square Error (STSA-log-MMSE) noise suppression; and wherein timing of the cardiac cycle based the acquired R wave onset is used to determine regions of acoustic inactivity as an input to STSA-log-MMSE.

* * * * *